(12) United States Patent
Gosain et al.

(10) Patent No.: US 9,535,010 B2
(45) Date of Patent: Jan. 3, 2017

(54) DEFECT SAMPLING FOR ELECTRON BEAM REVIEW BASED ON DEFECT ATTRIBUTES FROM OPTICAL INSPECTION AND OPTICAL REVIEW

(71) Applicant: KLA-Tencor Corporation, Milpitas, CA (US)

(72) Inventors: Rohan Gosain, San Jose, CA (US); Somit Joshi, Sunnyvale, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/709,390

(22) Filed: May 11, 2015

(65) Prior Publication Data
US 2015/0330912 A1 Nov. 19, 2015

Related U.S. Application Data

(60) Provisional application No. 61/993,631, filed on May 15, 2014.

(51) Int. Cl.
*G01N 21/00* (2006.01)
*G01N 21/88* (2006.01)
(Continued)

(52) U.S. Cl.
CPC ...... *G01N 21/8851* (2013.01); *G01N 21/9501* (2013.01); *G01N 23/2251* (2013.01); *G06T 7/001* (2013.01); *H01J 37/222* (2013.01); *H01L 22/12* (2013.01); *H01L 22/20* (2013.01); *G01N 2223/418* (2013.01);
(Continued)

(58) Field of Classification Search
CPC .......... G01N 21/88; G01N 21/95; H01J 37/22; G06T 7/00; G06F 17/50; G06F 19/00; H01L 21/66; G06K 9/00; G02B 27/40
See application file for complete search history.

(56) References Cited

U.S. PATENT DOCUMENTS 6,407,373 B1 * 6/2002 Dotan ................ G01N 21/9501
250/201.3
8,664,594 B1 3/2014 Jiang et al.
(Continued)

OTHER PUBLICATIONS

International Search Report for PCT/US2015/031002 mailed Aug. 25, 2015.
(Continued)

*Primary Examiner* — Tarifur Chowdhury
*Assistant Examiner* — Jamil Ahmed
(74) *Attorney, Agent, or Firm* — Ann Marie Mewherter

(57) ABSTRACT

Various embodiments for generating a defect sample for electron beam review are provided. One method includes combining, on a defect-by-defect basis, one or more first attributes for defects determined by optical inspection of a wafer on which the defects were detected with one or more second attributes for the defects determined by optical review of the wafer thereby generating combined attributes for the defects. The method also includes separating the defects into bins based on the combined attributes for the defects. The bins correspond to different defect classifications. In addition, the method includes sampling one or more of the defects for the electron beam review based on the bins into which the defects have been separated thereby generating a defect review sample for the electron beam review.

19 Claims, 3 Drawing Sheets

(51) Int. Cl.
- *G06T 7/00* (2006.01)
- *G01N 21/95* (2006.01)
- *H01J 37/22* (2006.01)
- *G01N 23/225* (2006.01)
- *H01L 21/66* (2006.01)

(52) U.S. Cl.
CPC . *G01N 2223/6466* (2013.01); *G01N 2223/66* (2013.01); *G06T 2207/30148* (2013.01); *H01J 2237/063* (2013.01); *H01J 2237/24592* (2013.01)

(56) References Cited

U.S. PATENT DOCUMENTS

| | | | |
|---|---|---|---|
| 8,692,204 B2 | 4/2014 | Kojima et al. | |
| 8,698,093 B1 | 4/2014 | Gubbens et al. | |
| 8,716,662 B1 | 5/2014 | MacDonald et al. | |
| 2004/0218806 A1* | 11/2004 | Miyamoto | G06K 9/6253 382/145 |
| 2007/0133860 A1* | 6/2007 | Lin | G06T 7/001 382/149 |
| 2008/0032429 A1* | 2/2008 | Chen | G01N 21/8851 438/14 |
| 2008/0058977 A1* | 3/2008 | Honda | G03F 1/0092 700/110 |
| 2011/0276935 A1* | 11/2011 | Fouquet | G06T 7/0006 716/112 |

OTHER PUBLICATIONS

Written Opinion of the International Searching Authority for PCT/US2015/031002 mailed Aug. 25, 2015.

* cited by examiner

DEFECT SAMPLING FOR ELECTRON BEAM REVIEW BASED ON DEFECT ATTRIBUTES FROM OPTICAL INSPECTION AND OPTICAL REVIEW

BACKGROUND OF THE INVENTION

1. Field of the Invention

The present invention generally relates to methods and systems for sampling defects for electron beam review by separating defects detected on a wafer into bins based on combined attributes from optical inspection and optical review and sampling the defects from the bins to generate a defect sample for the electron beam review.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Information beyond simple defect detection is often generated during inspection processes. For example, the detected defects are often classified into different groups. In one such example, after finding defects, they may be classified into different groups based on the defect characteristics such as size, magnitude, and location. In one particular example, using the information generated by optical wafer inspection, defects may be separated into cleanable and non-cleanable defects.

Defect classification often cannot be performed based on just images or information generated by a wafer inspection tool. In these instances, additional information may be generated using a defect review tool and defect classification is then determined based on the additional information. In some such instances, defects found by an optical defect finding apparatus may be reviewed using a high resolution scanning electron microscope (SEM) review tool. Defect review may, however, also be performed using an optical-based system. For example, laser-based defect review may be performed to verify a defect population detected by optical inspection.

In some instances, the optical review verified defect population may then be transferred to electron beam defect review. However, optical review is generally not capable of generating DOI type information for the verified defects. For instance, optical review may be capable of separating real defects from non-real defects (or "nuisances"), but not necessarily determining any DOI information for the real defects. Therefore, based on optical defect review results, the electron beam review tool may have no a priori knowledge of the nature of the defects included in the defect population to be reviewed.

In addition, as described above, an optical inspector may perform some defect classification that provides classification results (e.g., defect paretos), but those classification results generally have substantially limited accuracy and purity, particularly for defects that are near the threshold separating one defect classification from another. Therefore, any defect classification result generated by optical inspection may be provided to a defect review tool, but those defect classification results may not be particularly useful. Furthermore, the limited accuracy of defect classifications generated by optical inspection classifiers can result in ineffective troubleshooting of process tool excursions.

Electron beam based defect review that is performed using information generated by optical inspection or optical review may, therefore, have a number of disadvantages. For example, due to the limited information provided by optical inspection and optical review, electron beam review performed based on that information may have relatively low capture rates of actual defects. In addition, it would be difficult, if not impossible, to perform targeted DOI sampling for electron beam based defect review based on the defect information that is provided by optical inspection and optical review. Therefore, electron beam based review will take a relatively long time to produce ground truth defect classification results (e.g., ground truth paretos).

Accordingly, it would be advantageous to develop methods and systems for generating a defect sample for electron beam review that do not have one or more of the disadvantages described above.

SUMMARY OF THE INVENTION

The following description of various embodiments is not to be construed in any way as limiting the subject matter of the appended claims.

One embodiment relates to a computer-implemented method for generating a defect sample for electron beam review. The method includes combining, on a defect-by-defect basis, one or more first attributes for defects determined by optical inspection of a wafer on which the defects were detected with one or more second attributes for the defects determined by optical review of the wafer thereby generating combined attributes for the defects. The wafer is an unpatterned wafer. The method also includes separating the defects into bins based on the combined attributes for the defects. The bins correspond to different defect classifications. In addition, the method includes sampling one or more of the defects for electron beam review based on the bins into which the defects have been separated thereby generating a defect sample for the electron beam review. The combining, separating, and sampling steps are performed using a computer system.

Each of the steps of the method described above may be further performed as described herein. In addition, the method described above may include any other step(s) of any other method(s) described herein. Furthermore, the method described above may be performed by any of the systems described herein.

Another embodiment relates to a non-transitory computer-readable medium containing program instructions stored therein for causing a computer system to perform a computer-implemented method for generating a defect sample for electron beam review. The computer-implemented method includes the steps of the method described above. The computer-readable medium may be further configured as described herein. The steps of the method may be performed as described further herein. In addition, the method may include any other step(s) of any other method(s) described herein.

An additional embodiment relates to a system configured to generate a defect sample for electron beam review. The system includes an optical inspection subsystem configured to detect defects on a wafer. The system also includes an optical review subsystem configured to review defects detected on the wafer by the optical inspection subsystem. In addition, the system includes an electron beam review subsystem configured to review defects detected on the wafer by the optical inspection subsystem. The system also includes a computer subsystem configured for combining, on a defect-by-defect basis, one or more first attributes for the defects determined by the optical inspection subsystem with one or more second attributes for the defects determined by the optical review subsystem thereby generating combined attributes for the defects. The wafer is an unpatterned wafer. The computer subsystem is also configured for separating the defects into bins based on the combined attributes for the defects. The bins correspond to different defect classifications. The computer subsystem is further configured for sampling one or more of the defects for the review performed by the electron beam review subsystem based on the bins into which the defects have been separated thereby generating a defect sample for the review performed by the electron beam review subsystem. The system may be further configured according to any embodiment(s) described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
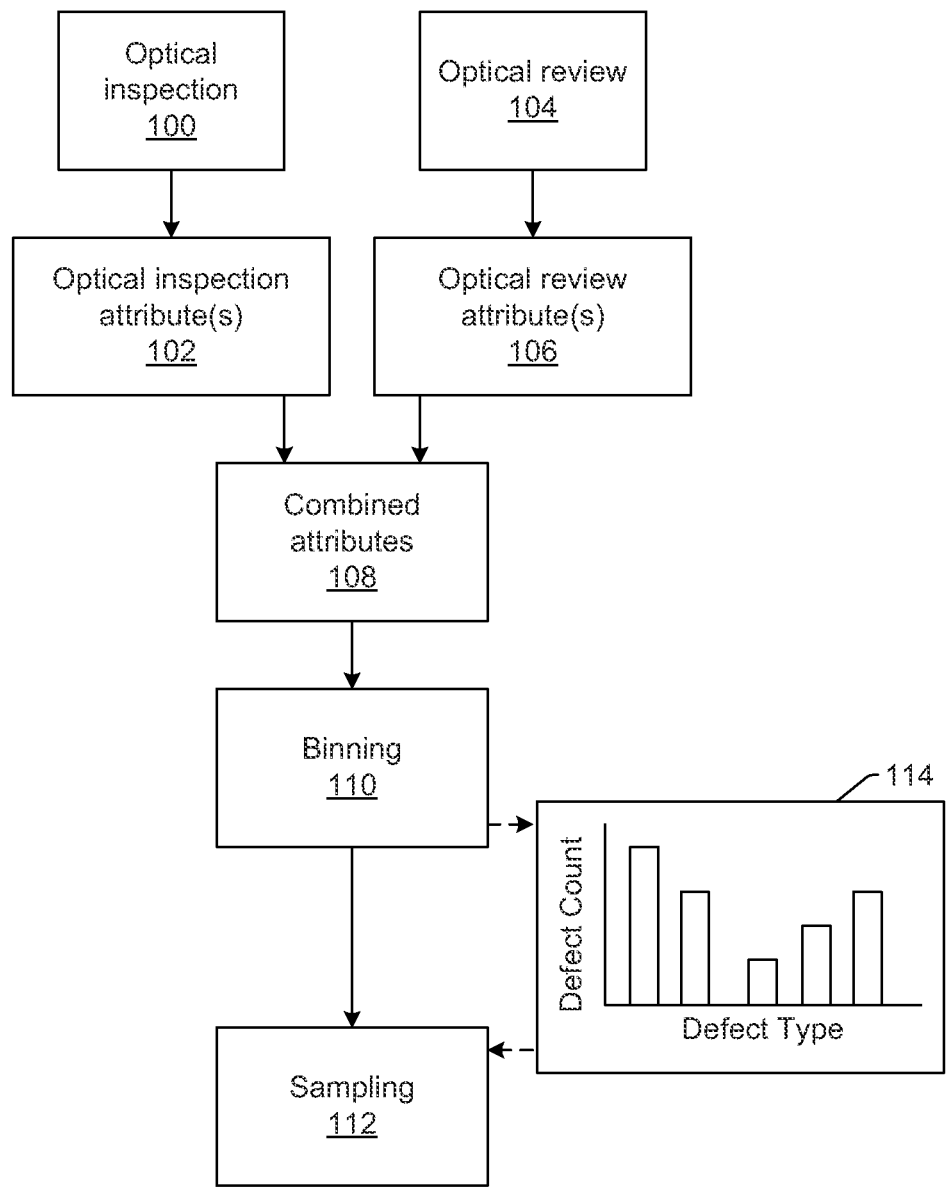
FIG. 1 is a flow chart illustrating one embodiment of a computer-implemented method for generating a defect sample for electron beam review.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a computer-implemented method for generating a defect sample for electron beam review. The embodiments described herein are generally configured for creating defect samples using a new automatic defect classifier that leverages defect attributes from optical review (e.g., laser-based review) and optical inspection (e.g., laser-based inspection). As will be described further herein, the embodiments provide an automated method for generating substantially high accuracy defect paretos after optical review. In addition, the embodiments provide a method for targeted defect of interest (DOI) sampling for electron beam based defect review (e.g., scanning electron microscopy (SEM) defect review). Therefore, the embodiments can be used to improve electron beam review capture rates and time to electron beam review paretos.

The method may include acquiring one or more first attributes for defects determined by optical inspection of a wafer on which the defects were detected. For example, as shown in FIG. 1, the method may include performing optical inspection 100 on a wafer, and the optical inspection results may include optical inspection attribute(s) 102, otherwise referred to herein as the first attribute(s). Acquiring the one or more first attributes may include actually performing optical inspection on the wafer (e.g., by performing inspection on the wafer using an optical inspection subsystem or system, which may be configured as described further herein). For example, acquiring the one or more first attributes may include scanning light over a wafer while detecting light from the wafer and then performing defect detection based on output (e.g., signals, signal data, images, image data) responsive to the detected light. That output may also be used to determine the one or more first attributes for the defects. In this manner, the one or more first attributes used in the embodiments described herein may be acquired by performing an inspection on the wafer. However, acquiring the one or more first attributes may not include performing an inspection process on the physical wafer. For example, acquiring one or more first attributes may include acquiring the one or more first attributes from a storage medium in which the one or more first attributes have been stored by another method or the optical inspection subsystem or system.

The method may also include acquiring one or more second attributes for defects determined by optical review of a wafer in which the defects that were detected by inspection are reviewed. For example, as shown in FIG. 1, the method may include performing optical review 104 on a wafer, and the optical inspection results may include optical review attribute(s) 106, otherwise referred to herein as the second attribute(s). Acquiring the one or more second attributes may include actually performing optical review on the wafer (e.g., by performing review on the wafer using an optical review subsystem or system, which may be configured as described further herein). For example, acquiring the one or more second attributes may include directing light to a reported location of a defect on a wafer while detecting light from the reported location and then relocating the defect on the wafer based on output (e.g., signals, signal data, images, image data) responsive to the detected light. That output may also be used to determine the one or more second attributes for the defect. In this manner, the one or more second attributes used in the embodiments described herein may be acquired by performing defect review on the wafer. However, acquiring the one or more second attributes may not include performing a defect review process on the physical wafer. For example, acquiring one or more second attributes may include acquiring the one or more second attributes from a storage medium in which the one or more second attributes have been stored by another method or the optical review subsystem or system.

In general, the term "inspection" is used herein to refer to a process performed on a wafer to inspect locations at which no defect information is previously available. In other words, an "inspection" process as described herein is not performed based on any a priori information about individual defects that are present on a wafer. In contrast, the term "review" is used herein to refer to a process performed on a wafer to examine locations on a wafer at which defects have been previously detected by another process ("an inspection process"). Therefore, unlike "inspection" processes, a "review" process is performed based on a priori information about the defects detected on a wafer that are being examined in the review process. Therefore, a review process cannot be performed on a wafer until an inspection process has been performed on the wafer. In addition, in instances such as those described herein in which two types of defect review, optical and electron beam, are performed on the same wafer, the wafer may be scanned for optical inspection, then optical review, and finally electron beam review. The types of scans that are performed in each process may be different from each other. For example, in an optical inspection, the entire wafer surface may be scanned through a rotational scan. In contrast, an optical review process may include an x-y type scan in which redetection of previously detected defects is attempted at only certain locations on the wafer.

The method includes combining, on a defect-by-defect basis, one or more first attributes for defects determined by optical inspection of a wafer on which the defects were detected with one or more second attributes for the defects determined by optical review of the wafer thereby generating combined attributes for the defects. For example, as shown in FIG. 1, optical inspection attribute(s) 102 and optical review attribute(s) 106 may be combined to generate combined attributes 108. In this manner, for any one defect detected on a wafer, its attribute(s) determined by optical inspection is/are combined with its attribute(s) determined by optical review. Therefore, the attribute(s) determined by inspection and review at the same within wafer location may be combined. As such, combining the attributes may include determining some offset or translation between wafer coordinates determined by the inspection and the review such that the attributes determined at the same or substantially the same within wafer location can be identified and then combined. Determining such an offset or translation may be performed in any suitable manner known in the art. The combined attributes may therefore be considered as a kind of attribute "superset" in which all of the combined attributes can be considered and used together for additional steps described herein.

The wafer is an unpatterned wafer. For example, the embodiments described herein are particularly useful for unpatterned wafers, which can be generally defined as wafers on which no patterned features (e.g., patterned device features and/or patterned test features) have been formed prior to inspection or wafers whose uppermost layer formed thereon does not contain any patterned features. The embodiments described herein may, therefore, be configured for unpatterned wafer defect sampling for electron beam review purposes.

Although many complex and advanced methods have been created for defect sampling for electron beam review of patterned wafers, the same is not necessarily true for unpatterned wafers. For instance, in many cases, information about defects detected on patterned wafers can be combined with information about the pattern formed on the wafers to intelligently sample defects that are of interest to a user. However, unpatterned wafers will obviously not include such pattern information. Therefore, sampling defects detected on unpatterned wafers remains relatively simple in comparison (e.g., random sampling, sampling based on clusters of defects, etc.). As such, sampling as many DOIs as possible on unpatterned wafers remains somewhat difficult. The embodiments described herein can, however, be used to provide such capability.

In one embodiment, the optical inspection includes laser-based wafer inspection. For example, the wafer inspection may be performed by illuminating the wafer with light generated by a laser. Such inspection may be performed by a system configured as described further herein.

In another embodiment, the optical review includes laser-based defect review. For example, the optical defect review may be performed by illuminating the wafer with light generated by a laser. Such defect review may be performed by a system configured as described further herein.

In some embodiments, the optical inspection and the optical review are performed by the same optical tool, and the optical inspection and the optical review are not performed with all of the same parameters on the same optical tool. For example, the optical inspection and review may be performed by one optical tool that has both inspection and review capability, which may be configured as described further herein. If the same tool is used for inspection and review, one or more parameters of the tool used for inspection should be different from one or more parameters of the tool used for review since the inspection and review are used to generate different information about defects and are used for different purposes (i.e., defect detection vs. redetection of previously detected defects). The parameters of the optical inspection and review may be different as described further herein.

In another embodiment, the optical inspection and the optical review are performed by two different, physically separate optical tools. Such different, physically separate optical tools may be further configured as described herein.

In one embodiment, the at least one of the one or more first attributes is complimentary to at least one of the one or more second attributes. For example, complimentary attributes from optical inspection can be selected and combined with optical review attributes to create an "attribute superset." In other words, the attribute superset may be created by selecting attribute(s) from optical inspection that provide complimentary defect information and combining the selected attribute(s) with attribute(s) from optical defect review.

The one or more first attributes that are used in the embodiments described herein may vary depending on the configuration of the optical inspection subsystem used to generate the one or more first attributes. For example, the optical inspection subsystems and tools described herein may have relatively good preferential collection by different channels based on DOI types with relatively limited granularity in patch defect images. Therefore, the first attribute(s) used in the embodiments described herein may be related to how the defects are detected by different channels of the inspection subsystem or system, but not necessarily any attributes determined from any one defect image generated by inspection. As such, creating the attribute supersets described herein may be performed by leveraging the preferential channel collection/detection of optical inspection.

In one such embodiment, the at least one first attribute includes a ratio of defect sizes determined by different channels of a tool used for the optical inspection. For example, one defect attribute that can be determined by inspection and may be complimentary to defect attributes from review includes a sizing ratio from multiple channels of an inspection subsystem or system, which may be configured as described further herein. In other words, the first attribute(s) may include a ratio of defect sizes as measured by different channels of an inspection system. In another such embodiment, the at least one first attribute includes information for which of two or more channels of a tool used for the optical inspection detected the defects. For example, one defect attribute that can be determined by inspection and may be complimentary to defect attributes from review includes preferential capture by specific channels of an inspection subsystem or system, which may be configured as described further herein. In other words, the first attribute(s) may be based on information about which defects are captured uniquely by a particular channel or set of channels.

In an additional such embodiment, the at least one first attribute and the at least one second attribute are determined with different wavelengths in the optical inspection and the optical review, and at least some of the defects include embedded defects. For example, information generated by different wavelengths of optical inspection (e.g., deep ultraviolet (DUV)) and optical review (e.g., blue wavelength(s)) may be leveraged to help classify embedded defects. "Embedded" defects is a term that is used to generally refer to defects that are located entirely below the upper surface of a wafer.

As with the one or more first attributes, the one or more second attributes that are used in the embodiments described herein may vary depending on the configuration of the optical review subsystem and systems used to generate the one or more second attributes. For example, the optical review subsystems and tools described herein may be capable of generating relatively data/information rich defect images and may also include a single channel. Therefore, the second attribute(s) used in the embodiments described herein may be determined from individual defect images generated by review.

In some embodiments, the one or more second attributes include size, shape, energy, orientation, location, or a combination thereof. For example, the embodiments described herein make use of one or more attributes in a defect attribute set created by optical review. Therefore, the embodiments described herein leverage the data or information rich images of defects that can be generated by optical review. Attributes that can be generated from such data rich images include, but are not limited to, size, shape, energy, and orientation. Such attributes may be determined from information generated by optical review in any suitable manner using any suitable method and/or algorithm. For example, defect size may be determined based on bounding box height and/or width (i.e., the dimensions of an imaginary box that surrounds the defect image portion within an optical review-generated image), defective pixel count (i.e., the number of pixels across which an image of a defect spans), and area. The shape attributes may include a characterization of the shape as resembling one of known defect shapes such as a "pointidot"-like shape, a "symmetric blob"-like shape, a residue-like shape, a scratch-like shape, etc. The energy attribute may be determined based on the scatter intensity of the defects in the optical review images. The orientation attribute may be used to separate scratches or residue of different orientations (e.g., right-to-left orientation vs. left-to-right orientation). The location attribute may include, for example, the radial location of the defects.

In another embodiment, the one or more second attributes include one or more quantifiable attributes extracted from images generated by the optical review. For example, the attributes determined by optical review may include any quantifiable attributes extracted from an optical image generated by an optical review subsystem or system, including those described above and/or any others that can be determined from optical review images.

The method also includes separating the defects into bins based on the combined attributes for the defects, and the bins correspond to different defect classifications. For example, the combination of the defect attribute(s) determined by optical inspection and the defect attribute(s) determined by optical review may be input into an attribute-based automatic defect classifier (ADC). Combining defect attributes from optical inspection and optical review provides quick and relatively accurate defect classifications.

In one such example, as shown in FIG. 1, combined attributes 108 generated from optical inspection attribute(s) 102 and optical review attribute(s) 106 may be input to binning step 110 in which the separating described herein may be performed. In this manner, the output of the separating step may include a number of the defects included in each of the bins (i.e., a bin-by-bin defect count) as a function of the different bins. Such output may be generally represented by a pareto chart or an optical-based ADC (oADC) pareto chart in the embodiments described herein or any other suitable output known in the art. For example, as shown in FIG. 1, the output of binning step 110 may include pareto chart 114. The different defect classifications of the different bins may vary depending on the wafer type and DOI types that vary from wafer-to-wafer. Some example of different defect classifications include, but are not limited to, particle (particle, large particle, small particle, etc.), embedded, residue, sphere, scratch, and polish-induced defects (PID).

Figure 2:
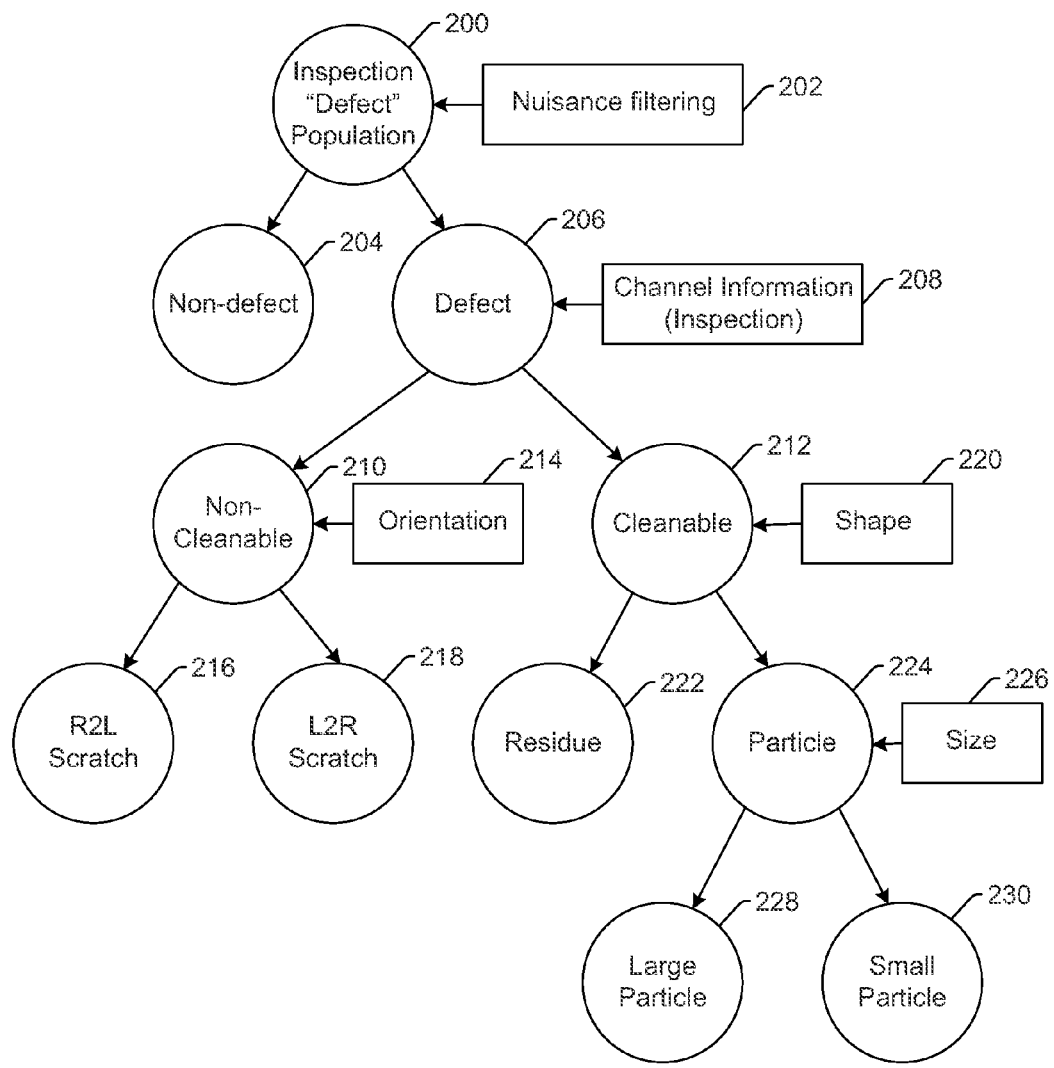
FIG. 2 is a flow chart illustrating one embodiment of separating defects into bins based on combined attributes for the defects that may be performed in method embodiments described herein.

The embodiment shown in FIG. 2 illustrates one way that the separating step described above may be performed using the combined attributes. Although some specific attributes and defect classifications are shown in FIG. 2, those specific attributes and defect classifications are not meant to limit the embodiments described herein in any way. Instead, those specific attributes and defect classifications are shown in this figure to further understanding of the embodiments, which as described herein may be based on a variety of different attributes and a variety of different bin classifications depending on the wafer type being inspected and reviewed.

As shown in FIG. 2, inspection "defect" population 200 may be input to the separating step. The inspection "defect" population may be generated by any of the inspections described herein (e.g., an optical inspection that includes a hot scan). As described herein, the inspection "defect" population may include a number of non-defects such as nuisances, noise, and other types of non-defects. Therefore, nuisance filtering 202 may be applied to the inspection "defect" population to preferably separate non-defects from actual or real defects. The nuisance filtering may be performed in any suitable manner known in the art. The results of the nuisance filtering may, therefore, include non-defect bin 204 and defect bin 206. The defects included in non-defect bin 204 may advantageously be eliminated from any other steps described herein.

The actual defects included in defect bin 206 may then be further separated based on the combined attributes determined for the defects as described herein. For example, channel information (inspection) 208 (i.e., which inspection channel(s) detected which defects) for the defects in defect bin 206 may be used to separate those defects into non-cleanable bin 210 and cleanable bin 212. Orientation attribute 214 for the defects in non-cleanable bin 210 may be used to separate the non-cleanable defects into right-to-left (R2L) scratch bin 216 and left-to-right (L2R) scratch bin 218. Shape attribute 220 for the defects in cleanable bin 212 may be used to separate those defects into residue bin 222 and particle bin 224. Size attribute 226 may be used to separate the defects in the particle bin into large particle bin 228 and small particle bin 230.

Therefore, in this embodiment, the separating step produces five bins that include R2L scratch bin 216, L2R scratch bin 218, residue bin 222, large particle bin 228, and small particle bin 230. The number of defects included in each of those bins may then be used to generate a pareto chart of the defect count as a function of bin. Information for which defects are included in each of the bins may then be used for the sampling step described further herein. In this manner, targeted DOI sampling for electron beam review may be performed based on the results of the separating step.

In one embodiment, the optical inspection includes performing a hot scan on the wafer and separating the defects detected by the hot scan from non-defects detected by the hot scan, the optical review is performed for at least some of the defects detected by the hot scan and none of the non-defects detected by the hot scan, and the combining is performed for at least some of the defects for which the optical review is performed and none of the non-defects. For example, the optical inspection can include running a hot scan with a greater than 0 nuisance rate. In a "hot" scan, the sensitivity of the wafer inspection may be setup to be the highest possible sensitivity. For example, the defect detection algorithm(s) and/or method(s) used for inspection of the wafer may be set to be the most sensitive possible. In one such example, if a defect detection algorithm compares the output of the optics of the inspector to a threshold (possibly after some processing is performed on the output), the threshold may be set to the lowest possible value thereby rendering the sensitivity of the tool to be the highest possible.

Separating the defects detected by the hot scan from non-defects may be performed using nuisance filtering. "Nuisance" or "nuisance defects" as those terms are used herein generally refer to "defects" that are detected by wafer inspection that are not actual defects on the wafer or are defects that a user does not care about (i.e., they are not DOIs). In this manner, "non-defects" as that term is used herein may include any nuisances, noise, or other detected events that are not really defects. In this manner, once the non-defects have been eliminated from the inspection results, the remaining, real defects may be input to optical review (in which one, some, or all of the "real" defects are reviewed). The combining step described herein may then be performed for only the defects that were optically reviewed, which would not include any of the non-defects detected by optical inspection. In this manner, the nuisance filtering and defect review classification results may be used in combination to help in creating real defect maps and other information that can then be used for electron beam review sampling as described herein.

The embodiments described herein can, therefore, enable hot scans on wafer inspection tools that will not overwhelm defect review with a prohibitive amount of nuisance defects. In particular, combining the nuisance filtering as described above with the defect classification information generated by optical defect review can be used to effectively reduce even huge amounts of nuisance defects detected in a hot scan. Therefore, hot scans can be used for routine wafer inspection without any of the normal disadvantages of such scans. As a result, the sensitivity that is used for routine wafer inspection may be the highest possible sensitivity even if that results in huge amounts of nuisance defects. In this manner, the embodiments described herein allow optical inspection tools to perform higher sensitivity scans with their current hardware. Achieving the same sensitivity enhancements through hardware developments could cost tens of millions of dollars. Therefore, the embodiments described herein can provide the same sensitivity enhancements at a much lower cost since hardware changes and improvements are not necessarily needed to implement the embodiments described herein.

The method further includes sampling one or more of the defects for electron beam review based on the bins into which the defects have been separated thereby generating a defect sample for the electron beam review. For example, as shown in FIG. 1, the method may include performing sampling step 112 based on results of binning 110, which may include pareto chart 114. Sampling the defect(s) may be performed as described further herein or in any other suitable manner known in the art (e.g., random sampling of a predetermined number of defects from each of the bins, sampling a predetermined number of the most diverse defects (i.e., defects having the most diversity in an attribute of the defects) in each of the bins, etc.).

In one embodiment, at least one of the bins corresponds to a DOI classification, and the sampling includes sampling from the at least one bin differently than sampling from other bins that do not correspond to the DOI classification. For example, the sampling may include sampling of targeted DOI (e.g., the DOI most interesting to a user) more heavily than sampling of other DOI. In this manner, the embodiments described herein may utilize a priori DOI knowledge (generated prior to electron beam review) to target some DOIs while skipping or avoiding others. In particular, the sampling rules may be based on specific DOI types. In one such example, based on the defects separated into the bins and their corresponding defect classifications created as described herein, rules may be used to preferentially sample specific DOIs (e.g., scratches and pits) and/or avoid some other DOIs (e.g., embedded defects). As such, typical electron beam non-visual defects (or SEM non-visuals, SNV) like embedded defects may not be selected for electron beam review. In this manner, the embodiments described herein may include targeted DOI sampling for review that is performed based on defect type information provided by an oADC classifier.

In some embodiments, the method includes performing the electron beam review for the sampled one or more defects to thereby generate defect classifications for the sampled one or more defects. Performing the electron beam review may include generating electron beam images of defects that can be redetected during defect review. One or more attributes of the defects that are redetected in the images may then be determined and used for classification of the defects. The one or more attributes may include any suitable attributes known in the art such as size, shape, orientation, texture, etc. and may be determined in any suitable manner using any suitable algorithm and/or method. Classification of the defects performed based on those attributes may be performed in much the same way as separating the defects into bins described herein. Since the defect classifications determined by electron beam review are typically performed based on electron beam images in which the defects are resolved, such defect classifications are generally referred to as "ground truth" classifications. The defect classification results generated by an electron beam review tool may be expressed in any suitable manner such as a pareto chart. Therefore, such a pareto chart may be commonly referred to as a ground truth pareto chart.

The embodiments described herein have, therefore, a number of advantages over previously used methods and systems for creating defect samples for electron beam review. For instance, the embodiments described herein provide actionable DOI information after optical review that can reduce the time needed to troubleshoot any process tool excursion. In addition, the sampling that is performed for electron beam review may include targeted DOI sampling based on the a priori DOI information provided after optical review. Such targeted DOI sampling can help in improving defect review capture rates and reducing the time involved in creating ground truth defect classification information (e.g., a ground truth pareto), which is advantageous for obvious reasons. For example, rules used for sampling may be set so that embedded defect types are not sampled for defect review since those defect types may not be visible to an electron beam review tool. Sampling only those defects that the defect review is capable of re-detecting will thereby increase the defect capture rate in defect review. In contrast, currently used methods for defect sampling on unpatterned wafers generally include making all optical review verified defects available for electron beam review and then randomly sampling a predetermined number (e.g., 100) of defects from those verified defects. However, those currently used methods do not provide any way for sampling targeted DOIs.

The combining, separating, and sampling steps described above are performed using a computer system, which may be configured as described further herein.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figure 3:
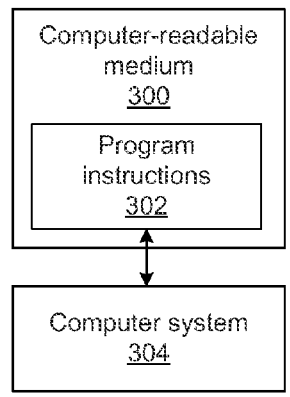
FIG. 3 is a block diagram illustrating one embodiment of a non-transitory computer-readable medium that includes program instructions executable on a computer system for performing one or more of the computer-implemented methods described herein.

An additional embodiment relates to a non-transitory computer-readable medium storing program instructions executable on a computer system for performing a computer-implemented method for generating a defect sample for electron beam review. One such embodiment is shown in FIG. 3. In particular, as shown in FIG. 3, computer-readable medium 300 includes program instructions 302 executable on computer system 304. The computer-implemented method includes the steps of the method described above. The computer-implemented method for which the program instructions are executable may include any other step(s) described herein.

Program instructions 302 implementing methods such as those described herein may be stored on computer-readable medium 300. The computer-readable medium may be a storage medium such as a magnetic or optical disk, or a magnetic tape or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 4:
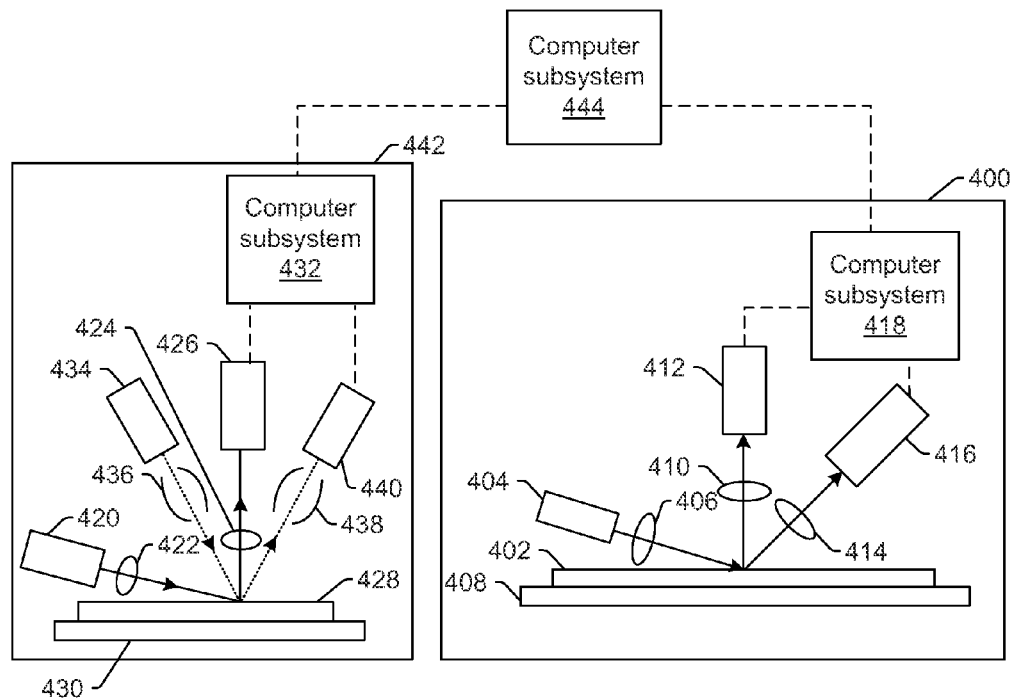
FIG. 4 is a schematic diagram illustrating a side view of one embodiment of a system configured to generate a defect sample for electron beam review.

An additional embodiment relates to a system configured to generate a defect sample for electron beam review. One embodiment of such a system is shown in FIG. 4. The system includes optical inspection subsystem 400 configured to detect defects on a wafer. As shown in FIG. 4, the optical inspection subsystem includes an illumination subsystem configured to direct light to wafer 402. The illumination subsystem includes at least one light source. For example, as shown in FIG. 4, the illumination subsystem includes light source 404. In one embodiment, the optical inspection subsystem is configured to detect the defects on the wafer by laser-based wafer inspection. For example, light source 404 may include a laser. The laser may include any suitable laser known in the art. The laser may be configured to generate light at any suitable wavelength(s) such as one or more DUV wavelengths. The light source may also include any other suitable light source known in the art.

In one embodiment, the illumination subsystem is configured to direct the light to the wafer at one or more angles of incidence that include at least an oblique angle of incidence. For example, as shown in FIG. 4, light from light source 404 is directed through lens 406 to wafer 402 at an oblique angle of incidence. Although lens 406 is shown in FIG. 4 as a single refractive optical element, it is to be understood that, in practice, lens 406 may include a number of refractive and/or reflective optical elements that in combination focus the light from the light source to the wafer. The oblique angle of incidence may include any suitable oblique angle of incidence, which may vary depending on, for instance, characteristics of the wafer and the defects to be detected on the wafer.

The illumination subsystem may be configured to direct the light to the wafer at different angles of incidence at different times. For example, the optical inspection subsystem may be configured to alter one or more parameters of one or more elements of the illumination subsystem such that the light can be directed to the wafer at an angle of incidence that is different than that shown in FIG. 4. In one such example, the optical inspection subsystem may be configured to move light source 404 and lens 406 such that the light is directed to the wafer at a different oblique angle of incidence or a normal (or near normal) angle of incidence.

The illumination subsystem may also or alternatively, in some instances, be configured such that the light can be directed to the wafer at multiple angles of incidence simultaneously. In one such example, the illumination subsystem may include another light source (not shown) and another lens (not shown) that are configured to direct light to the wafer at a different angle of incidence than that shown in FIG. 4. If such light is directed to the wafer at the same time as the other light, one or more characteristics (e.g., wavelength, polarization, etc.) of the light directed to the wafer at different angles of incidence may be different such that light resulting from illumination of the wafer at the different angles of incidence can be discriminated from each other at the detector(s). The illumination subsystem may have any other suitable configuration known in the art for directing the light to the wafer at multiple angles of incidence sequentially or simultaneously.

The illumination subsystem shown in FIG. 4 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the optical inspection system may be configured to alter one or more of the elements of the illumination subsystem based on the type of illumination to be used for inspection. For example, as described above, the optical inspection subsystem may be configured to alter one or more parameters of the illumination subsystem to alter the angle of incidence used for inspection. The optical inspection subsystem may be configured to alter the illumination subsystem in a similar fashion to change one or more other parameters (e.g., polarization, wavelength, etc.) of the illumination used for inspection.

The optical inspection subsystem also includes a scanning subsystem configured to cause the light to be scanned over the wafer. For example, the optical inspection subsystem may include stage 408 on which wafer 402 is disposed during inspection. The scanning subsystem may include any suitable mechanical and/or robotic assembly (that includes stage 408) that can be configured to move the wafer such that the light can be scanned over the wafer. In addition, or alternatively, the optical inspection subsystem may be configured such that one or more optical elements of the optical inspection subsystem perform some scanning of the light over the wafer. The light may be scanned over the wafer in any suitable fashion such as in a serpentine-like path or in a spiral path.

The optical inspection subsystem further includes one or more detection channels. For example, the optical inspection subsystem may be configured to detect surface defects with multiple collection/detection channels. At least one of the channels includes a detector configured to detect light from the wafer and to generate output responsive to the detected light. For example, the optical inspection subsystem shown in FIG. 4 includes two detection channels, one formed by collector 410 and detector 412 and another formed by collector 414 and detector 416. As shown in FIG. 4, the two detection channels are configured to collect and detect light at different scattering angles. In other words, both detection channels are configured to detect scattered light, and both detection channels are configured to detect light that is scattered at different angles from the wafer. The output generated by the detectors in response to the detected light may include any suitable output such as images, image data, signals, signal data, etc.

Although collectors 410 and 414 are shown in FIG. 4 as single refractive optical elements, it is to be understood that, in practice, collectors 410 and 414 may include a number of refractive and/or reflective optical elements that in combination focus the light from the wafer to their respective detectors. In addition, collectors 410 and 414 may have different configurations or the same configuration. Detectors 412 and 416 may include any suitable detectors known in the art such as photomultiplier tubes (PMTs). In addition, detectors 412 and 416 may have different configurations or the same configuration. The detection channels may also include any other suitable elements (not shown) such as polarizing component(s), spectral filter(s), spatial filter(s), reflective optical element(s), beam splitter(s), aperture(s), and the like, which may include any such suitable optical elements known in the art.

As further shown in FIG. 4, both detection channels are shown positioned in the plane of the paper and the illumination subsystem is also shown positioned in the plane of the paper. Therefore, in this embodiment, both detection channels are positioned in (e.g., centered in) the plane of incidence. However, one or more of the detection channels may be positioned out of the plane of incidence. For example, the detection channel formed by collector 414 and detector 416 may be configured to collect and detect light that is scattered out of the plane of incidence. Therefore, such a detection channel may be commonly referred to as a "side" channel, and such a side channel may be centered in a plane that is substantially perpendicular to the plane of incidence.

Although FIG. 4 shows an embodiment of the optical inspection subsystem that includes two detection channels, the optical inspection subsystem may include a different number of detection channels (e.g., only one detection channel or two or more detection channels). In one such instance, the detection channel formed by collector 414 and detector 416 may form one side channel as described above, and the optical inspection subsystem may include an additional detection channel (not shown) formed as another side channel that is positioned on the opposite side of the plane of incidence. In any case, each of the channels has its own collector, each of which is configured to collect light at different scattering angles than each of the other collectors.

As described further above, each of the detection channels included in the optical inspection subsystem may be configured to detect scattered light. Therefore, the optical inspection subsystem shown in FIG. 4 is configured for dark field (DF) inspection of wafers. In addition, the optical inspection subsystem may include one or more detection channels (not shown) that are configured for bright field (BF) inspection of wafers. In other words, the optical inspection subsystem may include one or more channels that are configured to detect light specularly reflected from the wafer. Therefore, the optical inspection subsystems described herein may be configured for DF and/or BF wafer inspection.

Computer subsystem 418 of the optical inspection subsystem is configured such that output generated by the detector(s) during scanning may be provided to computer subsystem 418. For example, the computer subsystem may be coupled to detectors 412 and 416 (e.g., by one or more transmission media shown by the dashed lines in FIG. 4, which may include any suitable transmission media known in the art) such that the computer subsystem may receive the output generated by the detectors. The computer subsystem may be configured to perform any step(s) using the output generated by the detector such as defect detection and generating an inspection results file for the wafer. Defect detection may be performed in any suitable manner (e.g., by applying one or more defect detection algorithms and/or methods to the output generated by the detectors, which may include any suitable algorithms and/or methods known in the art). Computer subsystem 418 may be further configured as described herein.

The one or more first attributes that may be determined by the optical inspection subsystem may include any such attributes described herein. For example, in one embodiment, the at least one first attribute includes a ratio of defect sizes determined by different channels of the optical inspection subsystem. For example, computer subsystem 418 may be configured to determine a first size of a defect using the output generated by one of the detectors and a second size of the same defect using the output generated by another of the detectors. In this manner, the output generated by more than one detector may be separately used to determine multiple defect sizes for the same defect. The computer subsystem may then determine a ratio of two or more of the defect sizes. This information may be useful in the embodiments described herein since defects may scatter light differently into different scattering angles, which results in different light scatter being detected by different detectors and therefore different defect sizes determined based on output generated by the different detectors. In addition, since different types of defects may scatter the light differently, the different defect sizes determined for any one defect may be reflective of the type of defect it is. Therefore, the defect size ratios described herein can be useful for separating one defect type from another.

In another embodiment, the at least one first attribute includes information for which of two or more channels of the optical inspection subsystem detected the defects. For example, at one location on a wafer, one detection channel of an optical inspection subsystem such as that shown in FIG. 4 may detect a defect while another channel of the same optical inspection subsystem may not detect a defect at the same location. In a different example, at one location on a wafer, more than one detection channel of an optical inspection subsystem such as that shown in FIG. 4 may detect a defect. Such discrepancies or similarities in the detection results produced using different channel output at the same location on a wafer may be due to the fact that different defect types may not scatter light into each of the channels equally. For example, some defect types preferentially scatter light into only certain scattering angles, which may therefore be detected by only certain channels of an inspection system. Therefore, based on knowledge about how a defect type scatters light into the scattering angles corresponding to the channels of an inspection system, information about which of the channels detected a defect at the same wafer location can be used to separate different types of defects into different bins. As such, information about which channels of an inspection system detected a defect may be useful as an attribute in the embodiments described herein.

In some embodiments, the optical inspection subsystem is configured to detect the defects on the wafer by performing a hot scan on the wafer and separating the defects detected by the hot scan from non-defects detected by the hot scan. The optical inspection subsystem may be configured to perform a hot scan on the wafer as described herein (e.g., using a threshold for defect detection that is substantially close to or at a noise floor of the output generated by a detector of the inspection system). The detection results produced by the hot scan can be separated into defects (real or actual defects) and non-defects (nuisance, noise, etc.) as described further herein.

The system also includes an optical review subsystem configured to review defects detected on the wafer by the optical inspection subsystem. For example, as shown in FIG. 4, the optical review subsystem includes light source 420, lens 422, collector 424, and detector 426. In this embodiment, light generated by light source 420 is directed to wafer 428 by lens 422. Light from the wafer due to illumination may be collected by collector 424 and directed to detector 426. In this manner, light source 420 and lens 422 may form an illumination channel of the optical review subsystem and the collector and the detector may form a detection channel of the optical review subsystem. Although the optical review subsystem is shown in FIG. 4 as including one illumination channel and one detection channel, the optical review subsystem may include more than one illumination channel and/or more than one detection channel.

In one embodiment, the optical review subsystem is configured to review the defects detected on the wafer by laser-based defect review. For example, light source 420 shown in FIG. 4 may be configured as a laser. The laser may include any suitable laser known in the art such as a single mode, fiber coupled diode laser. The laser may be configured to generate light having any suitable wavelength or wavelengths such as one or more wavelengths in the blue segment of the visible wavelength regime. As shown in FIG. 4, the light source and the lens may be configured to direct the light to the wafer at an oblique angle of incidence. However, the light source and the lens may be configured to direct the light to the wafer at any other suitable angle of incidence simultaneously or sequentially as described above with respect to the optical inspection subsystem. Lens 422 may be configured as described above with respect to the lens of the optical inspection subsystem. The illumination channel of the optical review subsystem may include any other element(s) not shown such as those described above with respect to the optical inspection subsystem.

Collector 424 may be configured as described above with respect to the collectors of the inspection subsystem. As shown in FIG. 4, collector 424 may be configured to detect light scattered from the wafer. In this manner, the light that is detected by detector 426 may include scattered light, and any images generated by the detector may be scattered light images. In addition, although collector 424 is shown in FIG. 4 as collecting light scattered at a normal angle or near normal angle(s) from the wafer, the collector may be configured to collect light scattered or reflected from the wafer at any other angle(s).

Detector 426 may be configured as an imaging detector. For example, the detector may be a charge coupled device (CCD) or a time delay integration (TDI) camera. The output generated by the detector in response to the detected light may include any suitable output such as images, image data, signals, signal data, etc. Preferably, the optical review subsystem is configured to generate images of defects being reviewed with a greater resolution than any images that can be generated by an inspection subsystem that detected the defects. In this manner, the optical review subsystem may be configured to generate the data and/or information rich images described herein such that one or more of the second attributes described herein can be determined from the images. The optical review subsystem may be configured to acquire images at variable integration times. The detection channel may also include any other suitable elements (not shown) such as polarizing component(s), spectral filter(s), spatial filter(s), reflective optical element(s), beam splitter(s), aperture(s), and the like, which may include any such suitable optical elements known in the art.

The optical review subsystem also includes a scanning subsystem configured to cause the light to be scanned over the wafer. For example, the optical review subsystem may include stage 430 on which wafer 428 is disposed during defect review. The scanning subsystem may include any suitable mechanical and/or robotic assembly (that includes stage 430) that can be configured to move the wafer such that the light can be scanned over the wafer. In addition, or alternatively, the optical review subsystem may be configured such that one or more optical elements of the optical review subsystem perform some scanning of the light over the wafer. The light may be scanned over the wafer in any suitable fashion such as in a serpentine-like path or in a spiral path.

Unlike the scanning subsystem of the inspection subsystem, which may be configured to scan the light over the entire wafer (or at least a substantial area on the wafer) in a substantially small amount of time, the scanning subsystem of the optical review subsystem may be configured for scanning the light over only discrete locations on the wafer at which the optical review is being performed for a subset of all of the defects detected on the wafer. Therefore, although the scanning subsystems of the inspection and optical review subsystems are described herein as possibly having the same or substantially similar configurations, the types of scanning performed by these scanning subsystems may, in fact, be very different.

Computer subsystem 432 is coupled to the optical review subsystem such that output generated by the detector may be provided to computer subsystem 432. For example, the computer subsystem may be coupled to detector 426 (e.g., by one or more transmission media shown by the dashed line in FIG. 4, which may include any suitable transmission media known in the art) such that the computer subsystem may receive the output generated by the detector. The computer subsystem may be configured to perform any step(s) using the output generated by the detector such as defect redetection and generating a defect review results file for the wafer. Defect redetection may be performed in any suitable manner (e.g., by applying one or more defect detection algorithms and/or methods to the output generated by the detector).

Computer subsystem 432 may be configured to determine one or more second attributes for the defects that are reviewed as described further herein. The one or more second attributes determined by the optical review subsystem may include any such attributes described herein. In one embodiment, the at least one first attribute and the at least one second attribute are determined with different wavelengths by the optical inspection subsystem and the optical review subsystem, and at least some of the defects include embedded defects. For example, the optical inspection subsystem may be configured to detect the defects with one or more DUV wavelengths and the optical review subsystem may be configured to perform defect review using one or more visible wavelengths (e.g., one or more blue wavelengths). Therefore, depending on the material composition of the wafer, the wavelength(s) used by wafer inspection may penetrate into the wafer while the wavelength(s) used for defect review may not (or vice versa). Alternatively, the different wavelengths used for inspection and defect review may penetrate into the wafer at different depths. Therefore, output generated for the defects with different wavelengths can reveal information about the defects such as their depth within or below an upper surface of the wafer. As such, comparing information for the defects detected at the different wavelengths, defects that are located at least partially below the upper surface of the wafer may be differentiated from defects that are located entirely above the upper surface of the wafer.

In some embodiments, the one or more second attributes include one or more quantifiable attributes extracted from images generated by the optical review subsystem. For example, as noted above, the detector of the optical review subsystem may be configured to generate images of the defects being reviewed. Those images may be used to determine any one or more quantifiable defect attributes as described further herein.

In another embodiment, the defects reviewed by the optical review subsystem include at least some of the defects detected by performing the hot scan and none of the non-defects detected by performing the hot scan. For example, as noted above, the inspection subsystem may be configured to detect "defects" by performing a hot scan on a wafer. The detected "defects" may be separated as described herein into defects (real or actual defects) and non-defects (nuisances, noise, etc.). The optical review subsystem may then be configured to perform defect review on only the defects (real or actual) or a sample of the defects (real or actual). The sample of defects that are reviewed by the defect review subsystem may be created in any suitable manner (e.g., by random sampling, diversity sampling, etc.).

The system shown in FIG. 4 also includes an electron beam review subsystem configured to review defects detected on the wafer by the optical inspection subsystem. The electron beam defect review subsystem shown in FIG. 4 includes an electron column coupled to a computer subsystem. The electron column includes electron beam source 434 configured to generate electrons that are focused to wafer 430 by one or more elements 436. The electron beam source may include, for example, a cathode source or emitter tip, and one or more elements 436 may include, for example, a gun lens, an anode, a beam limiting aperture, a gate valve, a beam current selection aperture, an objective lens, and a scanning subsystem, all of which may include any such suitable elements known in the art. Electrons returned from the wafer (e.g., secondary electrons) may be focused by one or more elements 438 to detector 440. One or more elements 438 may include, for example, a scanning subsystem, which may be the same scanning subsystem included in element(s) 436.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and 8,716,662 issued May 6, 2014 to MacDonald et al., which are incorporated by reference as if fully set forth herein. Although the electron column is shown in FIG. 4 as being configured such that the electrons are directed to the wafer at an oblique angle of incidence and are scattered from the wafer at another oblique angle, it is to be understood that the electron beam may be directed to and scattered from the wafer at any suitable angles.

Computer subsystem 432 may be coupled to detector 440 as described above. The detector may detect electrons returned from the surface of the wafer thereby forming electron beam images of the wafer. The electron beam images may include any of such images described herein. In one embodiment, the defects reviewed by the electron beam review subsystem include the sampled one or more defects, and the electron beam review subsystem is configured to generate defect classifications for the sampled one or more defects. For example, the images generated by detector 440 may be provided to computer subsystem 432 that determines a classification of the defects based on their electron beam images, which may be performed according to any of the embodiments described further herein. Computer subsystem 432 may be configured to perform any additional step(s) described herein and may be further configured as described herein.

As also shown in FIG. 4, computer subsystem 418 is included in the optical inspection subsystem, and computer subsystem 432 is coupled to the electron beam defect review subsystem and the optical review subsystem. Therefore, the electron beam and optical review subsystems may be configured to share a computer subsystem, which may be the case when the electron beam and optical review subsystems are included in a single tool (e.g., defect review tool 442). For example, in one embodiment, the optical review subsystem and the electron beam review subsystem are combined into one defect review tool. In one such embodiment, as shown in FIG. 4, the electron beam and optical review subsystems are configured such that both subsystems can generate output for a wafer while it is disposed on the same stage. In other words, the two subsystems may be configured to share a stage and the two subsystems may perform a process on a wafer simultaneously or sequentially. In addition, as shown in FIG. 4, the two subsystems may be configured to perform a process at the same location on the wafer simultaneously or sequentially. In other words, in the embodiment shown in FIG. 4, the optical review subsystem is configured to direct light to the same location that the electron beam review subsystem directs electrons to. However, in other embodiments, the two subsystems may be configured such that they both direct light and electrons to different locations on the wafer, which are spaced apart to some degree. In this manner, while the optical review subsystem is performing a process at one location on a wafer, the electron beam review subsystem can be performing a process at a different location on the same wafer. In either case, the two subsystems may be configured such that they are located within the same tool housing shown generally in FIG. 4 by the box surrounding these two subsystems.

In one embodiment, the optical inspection subsystem is configured as an inspection tool that is physically separated from the optical review subsystem and the electron beam review subsystem. For example, as shown in FIG. 4, optical inspection subsystem 400 is configured as an inspection tool, while the optical review subsystem and electron beam review subsystem are combined together in another tool. In addition, as shown in FIG. 4, the two tools may be physically separate and include their own stages and computer subsystems, as well as other separate components (not shown in FIG. 4) such as housings, power sources, etc. In addition, although the optical review subsystem and the electron beam review subsystem are shown in FIG. 4 are being combined into one tool, these two review subsystems may be alternatively configured as two separate tools in the same manner.

Since the attribute(s) determined by optical inspection are combined with attribute(s) determined by optical review as described herein, if the inspection tool is physically separate from the optical review subsystem, a data link may be created between the optical inspection tool and the optical review subsystem such that the defect attributes can be shared. For example, in the embodiment shown in FIG. 4, the system also includes computer subsystem 444 that is coupled to both computer subsystem 418 of the inspection subsystem and computer subsystem 432 included in defect review tool 442. Computer subsystem 444 may be configured to provide defect attribute(s) determined by computer subsystem 418 to computer subsystem 432 such that the inspection defect attribute(s) can be combined with defect attribute(s) determined by review. Computer subsystems 418 and 432 may, however, be coupled directly to each other, e.g., via a transmission medium or data link, or be coupled indirectly via a shared storage medium (not shown in FIG. 4), e.g., a fab database. In this manner, different computer subsystems may be coupled in a number of different ways such that the inspection defect attribute(s) and optical review defect attribute(s) can be combined by at least one of the computer subsystems.

The system also includes a computer subsystem configured for performing one or more steps of the method(s) described herein. This computer subsystem may be computer subsystem 418, 432, or 444 shown in FIG. 4. This computer subsystem may also be a computer subsystem included in either an optical defect review tool or an electron beam review tool if the two review subsystems are configured as separate tools as described above. In this manner, in some embodiments, the optical review subsystem and the computer subsystem are combined into one defect review tool. In other words, the computer subsystem that performs one or more steps of the method(s) described herein may be part of an optical defect review tool, which may also have electron beam review capability (as shown in FIG. 4). In this manner, the method may be performed "on-tool" by a defect review tool having at least optical review capability. In another embodiment, the electron beam review subsystem and the computer subsystem are combined into one defect review tool. In other words, the computer subsystem that performs one or more steps of the method(s) described herein may be part of an electron beam review tool, which may also have optical review capability (as shown in FIG. 4). In this manner, the method may be performed "on-tool" by a defect review tool having at least electron beam review capability. In yet another embodiment, the computer subsystem is not part of any tool that includes the subsystem(s) described herein. For example, the step(s) of the method(s) described herein may be performed by computer subsystem 444, which may be configured as a "stand-alone" type computer subsystem that is not part of an inspection and/or defect review tool. Each of the computer subsystems shown in FIG. 4 may be further configured as described herein.

In any case, one of the computer subsystems, included in the system, is configured for combining, on a defect-by-defect basis, one or more first attributes for the defects determined by the optical inspection subsystem with one or more second attributes for the defects determined by the optical review subsystem thereby generating combined attributes for the defects, which may be performed according to any of the embodiments described herein. The one or more first attributes and the one or more second attributes may include any of the first and second attributes described herein. In one embodiment, if the inspection includes a hot scan, the combining step is performed for at least some of the defects reviewed by the optical review subsystem and none of the non-defects detected by performing the hot scan. The computer subsystem is also configured for separating the defects into bins based on the combined attributes for the defects, which may be performed according to any of the embodiments described herein. The bins correspond to different defect classifications as described further herein. In addition, the computer subsystem is configured for sampling one or more of the defects for the review performed by the electron beam review subsystem based on the bins into which the defects have been separated thereby generating a defect sample for the review performed by the electron beam review subsystem, which may be performed according to any of the embodiments described herein.

In another embodiment, the optical inspection subsystem and the optical review subsystem are combined into one tool. In other words, the embodiments described herein can be implemented by combining optical inspection and optical review into one system. For example, the elements of the optical review subsystem shown in FIG. 4 may be moved into optical inspection subsystem 400 such that the two optical subsystems are combined into one tool. The optical review subsystem may be combined into the optical inspection subsystem in all of the ways described above with respect to defect review tool 442. For example, the optical inspection and review subsystems may be combined into the same tool such that they can simultaneously perform a process at the same location on the wafer, such that they can only sequentially perform a process at the same location on the wafer, such that they share the same stage, computer subsystem, and other elements such as a housing, power supply, etc.

In one such embodiment, the optical inspection subsystem is configured to detect the defects on the wafer using a first set of parameters, the optical review subsystem is configured to review the defects detected on the wafer using a second set of parameters, and at least one parameter in the first and second sets is different. For example, if the two optical subsystems are included in the same tool, they may share one or more (or even all) of the same elements. However, since the optical inspection subsystem and optical review subsystem are configured to generate dramatically different information for the wafer (i.e., defect detection information vs. defect review information), the optical inspection and review subsystems cannot use all of the same parameters to perform a process on the wafer.

In some instances, an optical inspection/review subsystem may be configured to change one or more illumination parameters such as wavelength(s), angle(s) of incidence, and polarization(s) and/or one or more detection parameters such as angle(s) of collection, polarization(s), integration times, etc. based on whether inspection or review is being performed by the system. All of these parameters may be changed in any suitable manner (e.g., by replacing one optical element such as a light source with a different optical element such as a different light source or by changing a parameter of an optical element that is used for both inspection and review such as a position of a collector that is used for both inspection and review). In addition, if the two optical subsystems are included in a single tool, but do not share any of the same optical elements, then the optical subsystems may be configured as two complete and separate optical subsystems that may or may not share the same stage, much in the same way that the two review subsystems are shown in FIG. 4 as being combined into one tool and yet not sharing any optical or electron beam components. The system embodiments described herein may be further configured according to any other embodiments described herein and may be configured to perform any step(s) of any method(s) described herein.

It is noted that FIG. 4 is provided herein to generally illustrate a configuration of an inspection system and defect review system that may be included in the system embodiments described herein. Obviously, the inspection and defect review system configurations described herein may be altered to optimize the performance of the inspection and defect review systems as is normally performed when designing commercial inspection and defect review systems. In addition, the systems described herein may be implemented using existing inspection systems and/or existing defect review systems (e.g., by adding functionality described herein to an existing inspection or defect review system) such as the Surfscan SPx series of tools and eDR series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention will be apparent to those skilled in the art in view of this description. For example, methods and systems for generating a defect sample for electron beam review are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to generate a defect sample for electron beam review, comprising:
   an optical inspection subsystem configured to detect defects on a wafer;
   an optical review subsystem configured to review defects detected on the wafer the optical inspection subsystem;
   an electron beam review subsystem configured to review defects detected on the wafer by the optical inspection subsystem; and
   a computer subsystem configured for:
   combining, on a defect-by-defect basis, one or more first attributes for the defects determined by the optical inspection subsystem with one or more second attributes for the defects determined by the optical review subsystem thereby generating combined attributes for the defects, wherein the wafer is an unpatterned wafer;
   separating the defects into bins based on the combined attributes for the defects, wherein the bins correspond to different defect classifications; and
   sampling one or more of the defects for the review performed by the electron beam review subsystem based on the bins into which the defects have been separated thereby generating a defect sample for the review performed by the electron beam review subsystem.

2. The system of claim 1, Wherein the optical inspection subsystem is further configured as an inspection tool that is physically separated from the optical review subsystem and the electron beam review subsystem.

3. The system of claim 1, wherein the optical inspection subsystem and the optical review subsystem are combined into one tool.

4. The system of claim 3, wherein the optical inspection subsystem is further configured to detect the defects on the wafer using a first set of parameters, wherein the optical review subsystem is further configured to review the defects detected on the wafer using a second set of parameters, and wherein at least one parameter in the first and second sets is different.

5. The system of claim 1, wherein the optical review subsystem and the electron beam review subsystem are combined into one defect review tool.

6. The system of claim 1, Wherein the optical review subsystem and the computer subsystem are combined into one defect review tool.

7. The system of claim 1, wherein the electron beam review subsystem and the computer subsystem are combined into one defect review tool.

8. The system of claim 1, wherein the computer subsystem is not part of any tool that comprises the optical inspection subsystem, optical review subsystem, or electron beam review subsystem.

9. The system of claim 1, wherein the optical inspection subsystem is further configured to detect the defects on the wafer by laser-based wafer inspection.

10. The system of claim 1, wherein the optical review subsystem is further configured to review the defects detected on the wafer by laser-based defect review.

11. The system of claim 1, wherein at least one of the one or more first attributes is complimentary to at least one of the one or more second attributes.

12. The system of claim 11, wherein the at least one first attribute comprises a ratio of defect sizes determined by different channels of the optical inspection subsystem.

13. The system of claim 11, wherein the at least one first attribute comprises information for which of two or more channels of the optical inspection subsystem detected the defects.

14. The system of claim 11, wherein the at least one first attribute and the at least one second attribute are determined with different wavelengths by the optical inspection subsystem and the optical review subsystem, and wherein at least some of the defects comprise embedded defects.

15. The system of claim 1, wherein the one or more second attributes comprise size, shape, energy, orientation, location, or a combination thereof.

16. The system of claim 1, wherein the one or more second attributes comprise one or more quantifiable attributes extracted from images generated by the optical review subsystem.

17. The system of claim 1, wherein the optical inspection subsystem is further configured to detect the defects on the wafer by performing a hot scan on the wafer and separating the defects detected by the hot scan from non-defects detected by the hot scan, wherein the defects reviewed by the optical review subsystem comprise at least some of the defects detected by performing the hot scan and none of the non-defects detected by performing the hot scan, and wherein said combining is performed for at least some of the defects reviewed by the optical review subsystem and none of the non-defects detected by performing the hot scan.

18. The system of claim 1, wherein at least one of the bins corresponds to a defect of interest classification, and wherein said sampling comprises sampling from the at least one bin differently than sampling from other bins that do not correspond to the defect of interest classification.

19. The system of claim 1, wherein the defects reviewed by the electron beam review subsystem comprise the sampled one or more defects, and wherein the electron beam review subsystem is further configured to generate defect classifications for the sampled one or more defects.

* * * * *